US012746081B2

(12) United States Patent
Tanabe et al.

(10) Patent No.: US 12,746,081 B2
(45) Date of Patent: Sep. 29, 2026

(54) ROBOTIC SURGICAL SYSTEM, CONTROL DEVICE OF ROBOTIC SURGICAL SYSTEM, AND CONTROL METHOD OF ROBOTIC SURGICAL SYSTEM

(71) Applicant: KAWASAKI JUKOGYO KABUSHIKI KAISHA, Kobe (JP)

(72) Inventors: Masataka Tanabe, Akashi (JP); Tetsuo Ichii, Kobe (JP); Ayataka Kobayashi, Kakogawa (JP); Yuichi Mizohata, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 446 days.

(21) Appl. No.: 18/248,064

(22) PCT Filed: Sep. 2, 2021

(86) PCT No.: PCT/JP2021/032366
§ 371 (c)(1),
(2) Date: Apr. 6, 2023

(87) PCT Pub. No.: WO2022/074978
PCT Pub. Date: Apr. 14, 2022

(65) Prior Publication Data

US 2023/0270515 A1 Aug. 31, 2023

(30) Foreign Application Priority Data

Oct. 9, 2020 (JP) ................................ 2020-171024

(51) Int. Cl.
*A61B 34/37* (2016.01)
*A61B 34/00* (2016.01)

(52) U.S. Cl.
CPC ........ *A61B 34/37* (2016.02); *A61B 2034/742* (2016.02)

(58) Field of Classification Search
CPC ... A61B 2034/742; A61B 34/30; A61B 34/35; A61B 34/37; A61B 90/05
See application file for complete search history.

(56) References Cited

U.S. PATENT DOCUMENTS

| | | | | | |
|---|---|---|---|---|---|
| 6,092,004 | A * | 7/2000 | Harima | G05B 19/4103 700/250 |
| 2009/0326552 | A1* | 12/2009 | Diolaiti | A61B 90/10 606/130 |
| 2011/0309782 | A1* | 12/2011 | Bonin | H02P 6/15 318/611 |
| 2018/0014897 | A1 | 1/2018 | Peine | |
| 2019/0374299 | A1 | 12/2019 | Peine | |
| 2020/0261169 | A1 | 8/2020 | Miller et al. | |
| 2022/0273385 | A1 | 9/2022 | Peine | |

FOREIGN PATENT DOCUMENTS

| | | | |
|---|---|---|---|
| JP | S61-123907 | A | 6/1986 |
| JP | 2018-505739 | A | 3/2018 |
| JP | 2019-202383 | A | 11/2019 |
| WO | 2019/032309 | A2 | 2/2019 |

* cited by examiner

*Primary Examiner* — Scott Luan
(74) *Attorney, Agent, or Firm* — METROLEX IP LAW GROUP, PLLC; Robert L. Scott, Esq.

(57) ABSTRACT

A robotic surgical system includes a controller configured or programmed to limit a speed command value within a range of a speed limit value, and limit an acceleration command value within a range of an acceleration limit value.

10 Claims, 11 Drawing Sheets

ROBOTIC SURGICAL SYSTEM, CONTROL DEVICE OF ROBOTIC SURGICAL SYSTEM, AND CONTROL METHOD OF ROBOTIC SURGICAL SYSTEM

TECHNICAL FIELD

The present invention relates to a robotic surgical system, a control device of a robotic surgical system, and a control method of a robotic surgical system, and more particularly, it relates to a robotic surgical system, a control device of a robotic surgical system, and a control method of a robotic surgical system to control the operation of a surgical instrument based on an operation received by an operation unit.

BACKGROUND ART

Conventionally, a robotic surgical system including an arm, a tool (surgical instrument) connected to an end of the arm, and an input handle (operation unit) is known. For example, in a robotic surgical system described in Japanese Translation of PCT International Application Publication No 2018-505739, movement of a surgical instrument is controlled based on the amount of operation received by an operation unit. The surgical instrument moves within the body of a patient, which is a surgical site.

PRIOR ART

Patent Document

Patent Document 1: Japanese Translation of PCT International Application Publication No 2018-505739

SUMMARY OF THE INVENTION

However, conventionally, there is room for improvement in terms of protection of components such as motors included in arm joints and reduction or prevention of arm vibrations. For example, when the amount of operation received by an input handle is large, the amount of movement of an arm per unit time becomes large. In this case, the motors provided at the arm joints may rotate at an excessively high speed, and components of the motors may be damaged. Furthermore, the arm may vibrate due to the large amount of movement of the arm per unit time.

The present disclosure is intended to solve the above problems. The present disclosure aims to provide a robotic surgical system, a control device of a robotic surgical system, and a control method of a robotic surgical system each capable of protecting components of joints of a manipulator arm and reducing or preventing vibrations of the manipulator arm.

In order to attain the aforementioned object, a robotic surgical system according to a first aspect of the present disclosure includes a patient-side apparatus including a manipulator arm having a tip end side to which a surgical instrument is attached, an operator-side apparatus including an operation unit to receive an operation on the surgical instrument, and a controller configured or programmed to calculate a speed command value and an acceleration command value to operate the surgical instrument based on the received operation, and control operation of the surgical instrument based on the speed command value and the acceleration command value. The controller is configured or programmed to limit the speed command value within a range of a speed limit value, and limit the acceleration command value within a range of an acceleration limit value.

In the robotic surgical system according to the first aspect of the present disclosure, as described above, the controller is configured or programmed to limit the speed command value within the range of the speed limit value, and limit the acceleration command value within the range of the acceleration limit value. Accordingly, even when the amount of operation received by the operation unit is relatively large, both the speed command value and the acceleration command value are limited, and thus an increase in the amount of movement of the manipulator arm per unit time is reduced or prevented. Therefore, rotation of motors provided at joints of the manipulator arm at an excessively high speed is reduced or prevented, and thus components of the joints of the manipulator arm, such as the motors, can be protected. Furthermore, an increase in the amount of movement of the manipulator arm per unit time is reduced or prevented, and thus vibrations of the manipulator arm due to the large amount of movement of the manipulator arm per unit time can be reduced or prevented. Consequently, the components of the joints of the manipulator arm can be protected, and the vibrations of the manipulator arm can be reduced or prevented.

A control device of a robotic surgical system according to a second aspect of the present disclosure is a control device of a robotic surgical system including a patient-side apparatus including a manipulator arm having a tip end side to which a surgical instrument is attached, and an operator-side apparatus including an operation unit to receive an operation on the surgical instrument, and includes a controller configured or programmed to calculate a speed command value and an acceleration command value to operate the surgical instrument based on the received operation, and control operation of the surgical instrument based on the speed command value and the acceleration command value. The controller is configured or programmed to limit the speed command value within a range of a speed limit value, and limit the acceleration command value within a range of an acceleration limit value.

In the control device of the robotic surgical system according to the second aspect of the present disclosure, as described above, the controller is configured or programmed to limit the speed command value within the range of the speed limit value, and limit the acceleration command value within the range of the acceleration limit value. Accordingly, even when the amount of operation received by the operation unit is relatively large, both the speed command value and the acceleration command value are limited, and thus an increase in the amount of movement of the manipulator arm per unit time is reduced or prevented. Therefore, rotation of motors provided at joints of the manipulator arm at an excessively high speed is reduced or prevented, and thus components of the joints of the manipulator arm, such as the motors, can be protected. Furthermore, an increase in the amount of movement of the manipulator arm per unit time is reduced or prevented, and thus vibrations of the manipulator arm due to the large amount of movement of the manipulator arm per unit time can be reduced or prevented. Consequently, it is possible to provide the control device of the robotic surgical system capable of protecting the components of the joints of the manipulator arm and reducing or preventing the vibrations of the manipulator arm.

A control method of a robotic surgical system according to a third aspect of the present disclosure is a control method of a robotic surgical system including a patient-side apparatus including a manipulator arm having a tip end side to which a surgical instrument is attached, and an operator-side apparatus including an operation unit to receive an operation on the surgical instrument, and includes receiving an operation on the surgical instrument, and calculating a speed command value and an acceleration command value to operate the surgical instrument based on the received operation, and controlling operation of the surgical instrument based on the speed command value and the acceleration command value. The controlling the operation of the surgical instrument based on the speed command value and the acceleration command value includes limiting the speed command value within a range of a speed limit value, and limiting the acceleration command value within a range of an acceleration limit value.

In the control method of the robotic surgical system according to the third aspect of the present disclosure, as described above, the controlling the operation of the surgical instrument based on the speed command value and the acceleration command value includes the limiting the speed command value within the range of the speed limit value, and the limiting the acceleration command value within the range of the acceleration limit value. Accordingly, even when the amount of operation received by operation unit is relatively large, both the speed command value and the acceleration command value are limited, and thus an increase in the amount of movement of the manipulator arm per unit time is reduced or prevented. Therefore, rotation of motors provided at joints of the manipulator arm at an excessively high speed is reduced or prevented, and thus components of the joints of the manipulator arm, such as the motors, can be protected. Furthermore, an increase in the amount of movement of the manipulator arm per unit time is reduced or prevented, and thus vibrations of the manipulator arm due to the large amount of movement of the manipulator arm per unit time can be reduced or prevented. Consequently, it is possible to provide the control method of the robotic surgical system capable of protecting the components of the joints of the manipulator arm and reducing or preventing the vibrations of the manipulator arm.

According to the present disclosure, as described above, it is possible to protect the components of the joints of the manipulator arm and reduce or prevent the vibrations of the manipulator arm.

MODES FOR CARRYING OUT THE INVENTION

Figure 1:
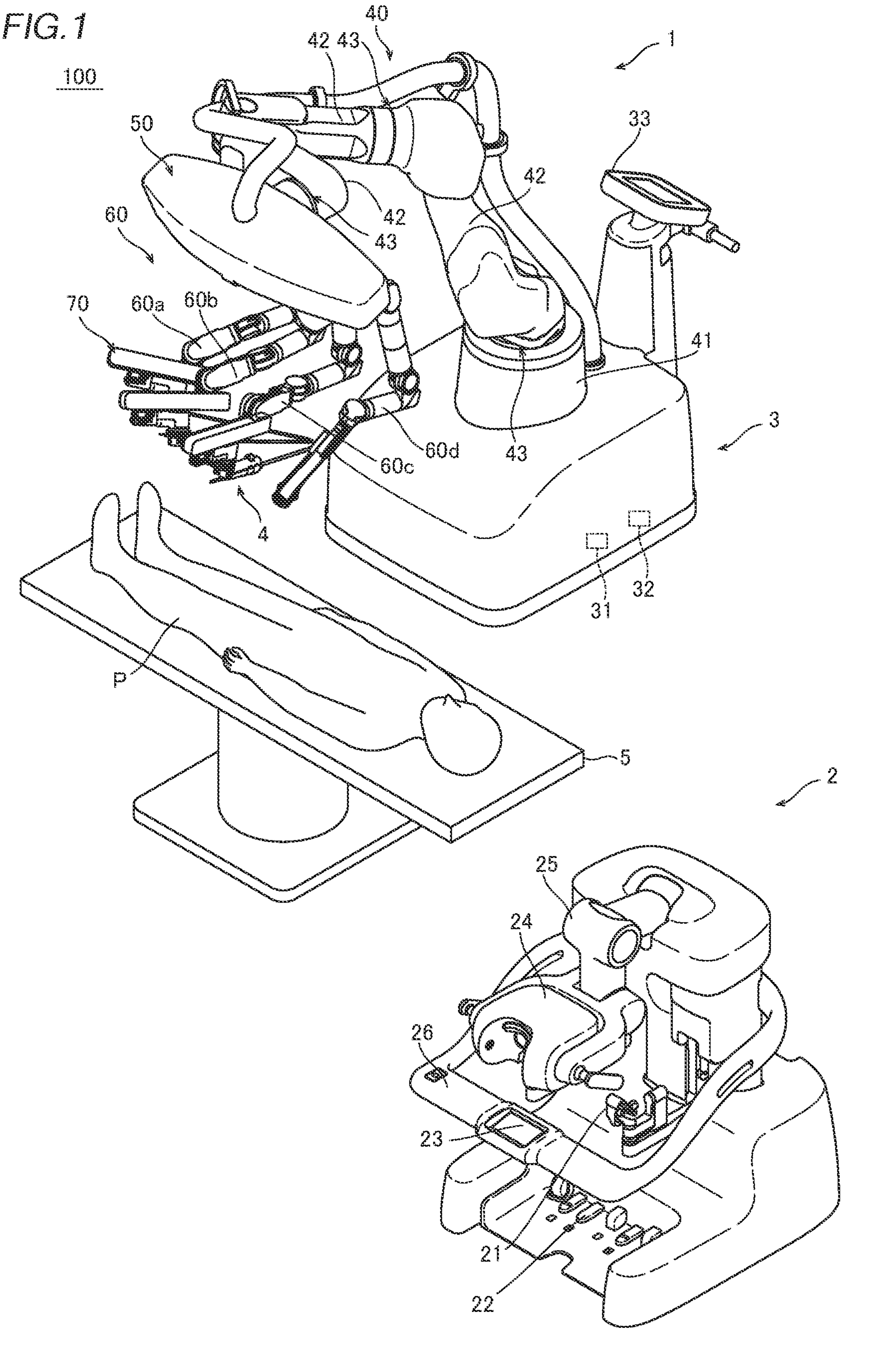
FIG. 1 is a diagram showing the configuration of a surgical system according to an embodiment of the present disclosure.

An embodiment embodying the present disclosure is hereinafter described on the basis of the drawings.

The configuration of a surgical system 100 according to this embodiment is now described with reference to FIGS. 1 to 16. The surgical system 100 includes a medical manipulator 1 that is a patient P-side apparatus and a remote control apparatus 2 that is an operator-side apparatus to operate the medical manipulator 1. The medical manipulator 1 includes a medical cart 3 and is movable. The remote control apparatus 2 is spaced apart from the medical manipulator 1, and the medical manipulator 1 is remotely operated by the remote control apparatus 2. A surgeon inputs a command to the remote control apparatus 2 to cause the medical manipulator 1 to perform a desired operation. The remote control apparatus 2 transmits the input command to the medical manipulator 1. The medical manipulator 1 operates based on the received command. The medical manipulator 1 is arranged in an operating room that is a sterilized sterile field. The surgical system 100 is an example of a "robotic surgical system" in the claims.

The remote control apparatus 2 is arranged inside or outside the operating room, for example. The remote control apparatus 2 includes operation manipulator arms 21, operation pedals 22, a touch panel 23, a monitor 24, a support arm 25, and a support bar 26. The operation manipulator arms 21 include operation handles for the surgeon to input commands. The operation manipulator arms 21 receive the amount of operation for a surgical instrument 4. The monitor 24 is a scope-type display that displays an image captured by an endoscope. The support arm 25 supports the monitor 24 so as to align the height of the monitor 24 with the height of the surgeon's face. The touch panel 23 is arranged on the support bar 26. The surgeon's head is detected by a sensor (not shown) provided in the vicinity of the monitor 24 such that the medical manipulator 1 can be operated by the remote control apparatus 2. The surgeon operates the operation manipulator arms 21 and the operation pedals 22 while visually recognizing an affected area on the monitor 24. Thus, a command is input to the remote control apparatus 2. The command input to the remote control apparatus 2 is transmitted to the medical manipulator 1. The operation manipulator arms 21 are examples of an "operation unit" in the claims.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote control apparatus 2. The controller 31 is an example of a "control device of a robotic surgical system" in the claims.

The medical cart 3 includes an input 33. The input 33 receives operations to move a positioner 40, an arm base 50, and a plurality of manipulator arms 60 or change their postures mainly in order to prepare for surgery before the surgery.

Figure 2:
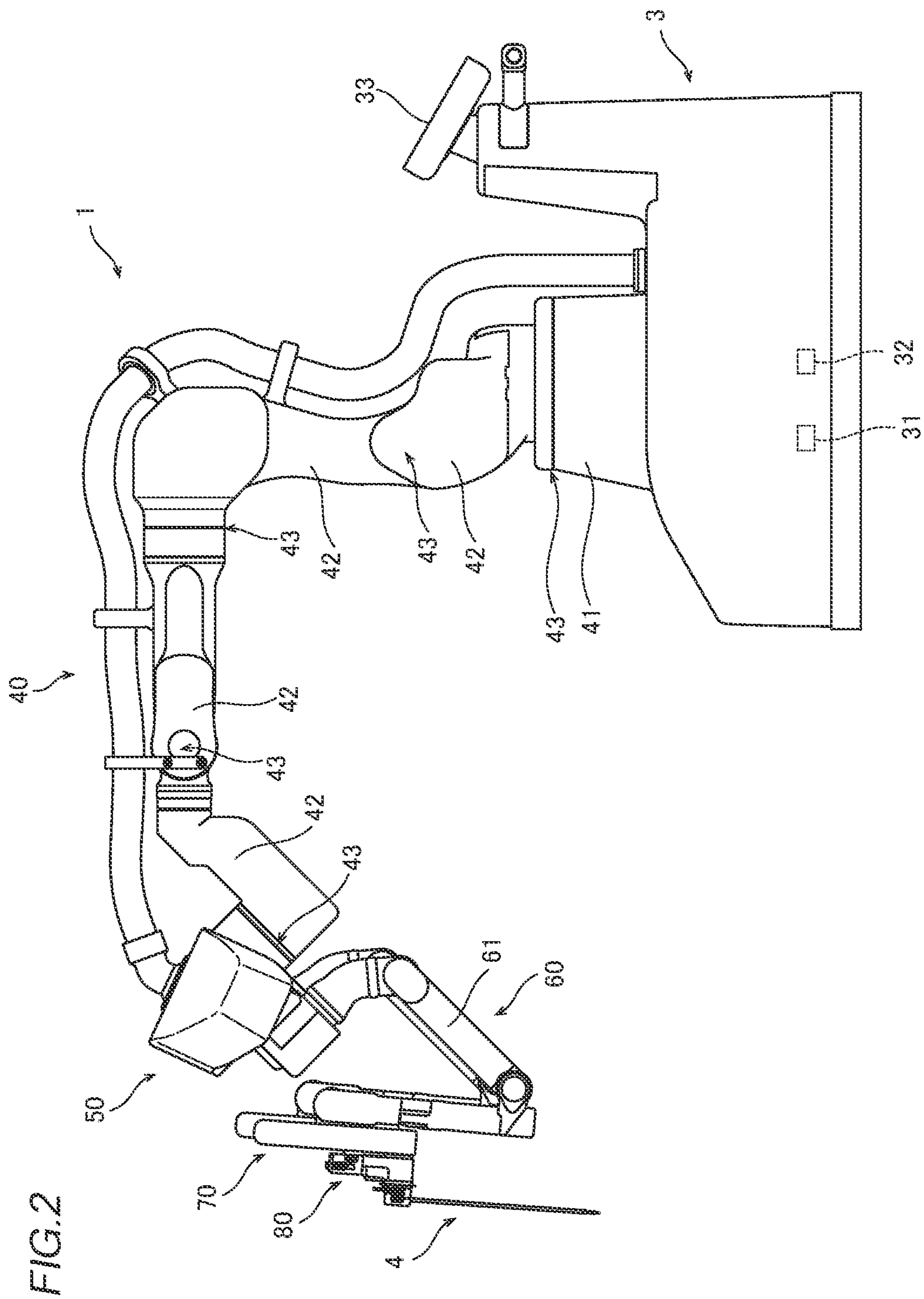
FIG. 2 is a diagram showing the configuration of a medical manipulator according to the embodiment of the present disclosure.

The medical manipulator 1 shown in FIGS. 1 and 2 is arranged in the operating room. The medical manipulator 1 includes the medical cart 3, the positioner 40, the arm base 50, and the plurality of manipulator arms 60. The arm base 50 is attached to the tip end of the positioner 40. The arm base 50 has a relatively long rod shape (long shape). The bases of the plurality of manipulator arms 60 are attached to the arm base 50. Each of the plurality of manipulator arms 60 is able to take a folded posture (stored posture). The arm base 50 and the plurality of manipulator arms 60 are covered with sterile drapes (not shown) and used.

The positioner 40 includes a 7-axis articulated robot, for example. The positioner 40 is arranged on the medical cart 3. The positioner 40 moves the arm base 50. Specifically, the positioner 40 moves the position of the arm base 50 three-dimensionally.

The positioner 40 includes a base 41 and a plurality of links 42 coupled to the base 41. The plurality of links 42 are coupled to each other by joints 43.

As shown in FIG. 1, the surgical instrument 4 is attached to the tip end of each of the plurality of manipulator arms 60. The surgical instrument 4 includes a replaceable instrument or an endoscope 6 (see FIG. 6), for example.

Figure 3:
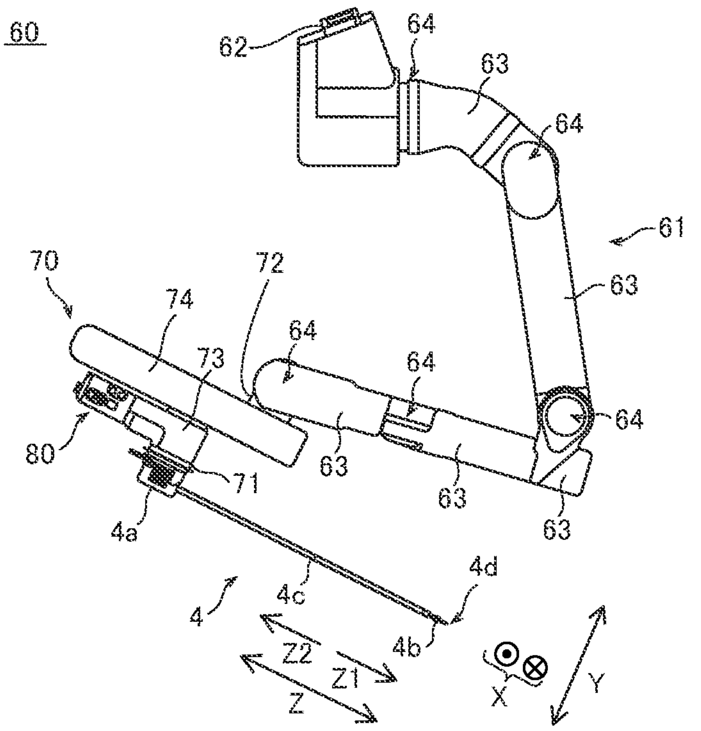
FIG. 3 is a diagram showing the configuration of a manipulator arm according to the embodiment of the present disclosure.

As shown in FIG. 3, the instrument includes a driven unit 4*a* driven by servomotors M2 provided in a holder 71 of each of the manipulator arms 60. A pair of forceps 4*b* is provided at the tip end of the instrument. The pair of forceps 4*b* is an example of an "end effector" in the claims.

Figure 4:
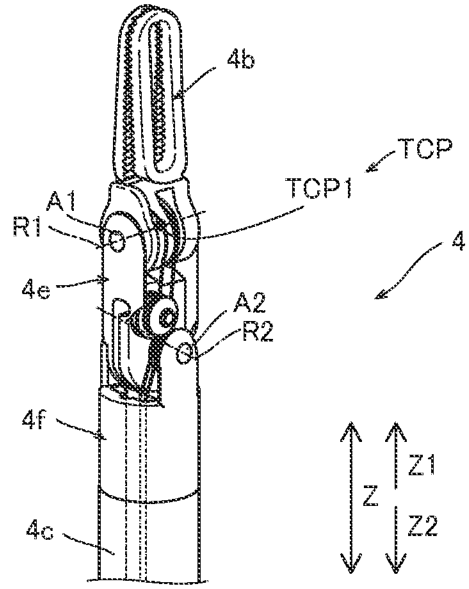
FIG. 4 is a diagram showing a pair of forceps.

As shown in FIG. 4, the instrument includes a first support 4*e* that supports the pair of forceps 4*b* such that the pair of forceps 4*b* is rotatable about a first axis A1, a second support 4*f* that supports the first support 4*e* such that the first support 4*e* is rotatable about a second axis A2, and a shaft 4*c* connected to the second support 4*f*. The driven unit 4*a*, the shaft 4*c*, the second support 4*f*, the first support 4*e*, and the pair of forceps 4*b* are arranged along a Z direction.

The pair of forceps 4*b* is attached to the first support 4*e* so as to rotate about the rotation axis line R1 of the first axis A1. The second support 4*f* supports the first support 4*e* such that the first support 4*e* is rotatable about the second axis A2. That is, the first support 4*e* is attached to the second support 4*f* so as to rotate about the rotation axis line R2 of the second axis A2. A portion of the first support 4*e* on the tip end side (Z1 direction side) has a U-shape. A tool center point (TCP1) is set at the center of the U-shaped portion of the first support 4*e* on the tip end side in a rotation axis R1 direction.

Figure 6:
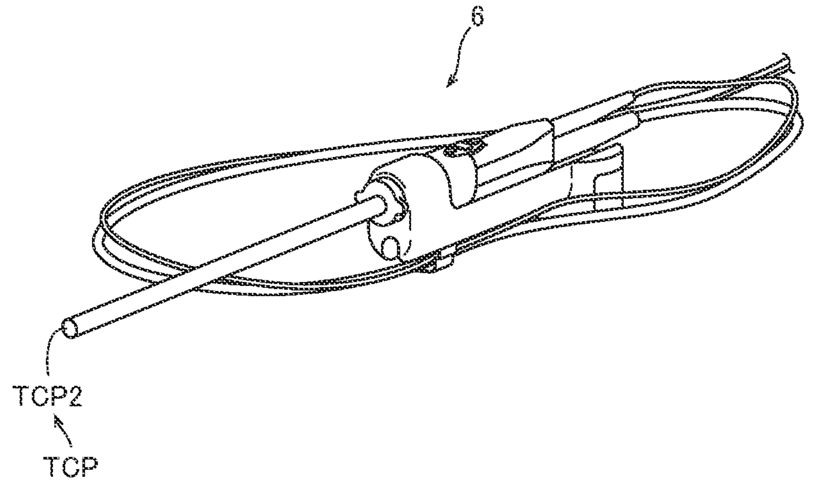
FIG. 6 is a diagram showing an endoscope.
Figure 7:
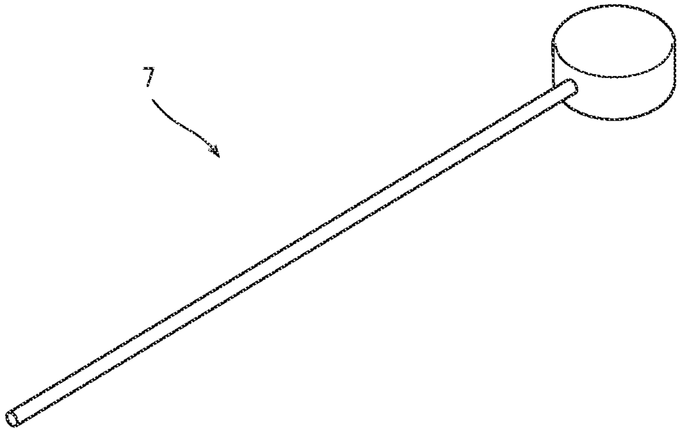
FIG. 7 is a diagram showing a pivot position teaching instrument.

As shown in FIG. 6, a TCP2 of the endoscope 6 is set at the tip end of the endoscope 6.

The configuration of the manipulator arms 60 is now described in detail.

As shown in FIG. 3, each of the manipulator arms 60 includes an arm portion 61 (a base 62, links 63, and joints 64) and a translation mechanism 70 provided at the tip end of the arm portion 61. The tip end sides of the manipulator arms 60 three-dimensionally move with respect to the base sides (arm base 50) of the manipulator arms 60. The plurality of manipulator arms 60 have the same configuration as each other.

The translation mechanism 70 is provided on the tip end side of the arm portion 61, and the surgical instrument 4 is attached thereto. The translation mechanism 70 translates the surgical instrument 4 in a direction in which the surgical instrument 4 is inserted into a patient P. Furthermore, the translation mechanism 70 translates the surgical instrument 4 relative to the arm portion 61. Specifically, the translation mechanism 70 includes the holder 71 that holds the surgical instrument 4. The servomotors M2 (see FIG. 10) are housed in the holder 71. The servomotors M2 rotate rotary bodies provided in the driven unit 4*a* of the surgical instrument 4. The rotary bodies of the driven unit 4*a* are rotated such that the pair of forceps 4*b* is operated.

The arm portion 61 includes a 7-axis articulated robot arm. The arm portion 61 includes the base 62 to attach the arm portion 61 to the arm base 50, and a plurality of links 63 coupled to the base 62. The plurality of links 63 are coupled to each other by the joints 64.

The translation mechanism 70 translates the surgical instrument 4 attached to the holder 71 along the Z direction (a direction in which the shaft 4*c* extends) by translating the holder 71 along the Z direction. Specifically, the translation mechanism 70 includes a base end side link 72 connected to the tip end of the arm portion 61, a tip end side link 73, and a coupling link 74 provided between the base end side link 72 and the tip end side link 73. The holder 71 is provided on the tip end side link 73.

The coupling link 74 of the translation mechanism 70 is configured as a double speed mechanism that moves the tip end side link 73 relative to the base end side link 72 along the Z direction. The tip end side link 73 is moved along the Z direction relative to the base end side link 72 such that the surgical instrument 4 provided on the holder 71 is translated along the Z direction. The tip end of the arm portion 61 is connected to the base end side link 72 so as to rotate the base end side link 72 about an X direction orthogonal to the Z direction.

Figure 5:
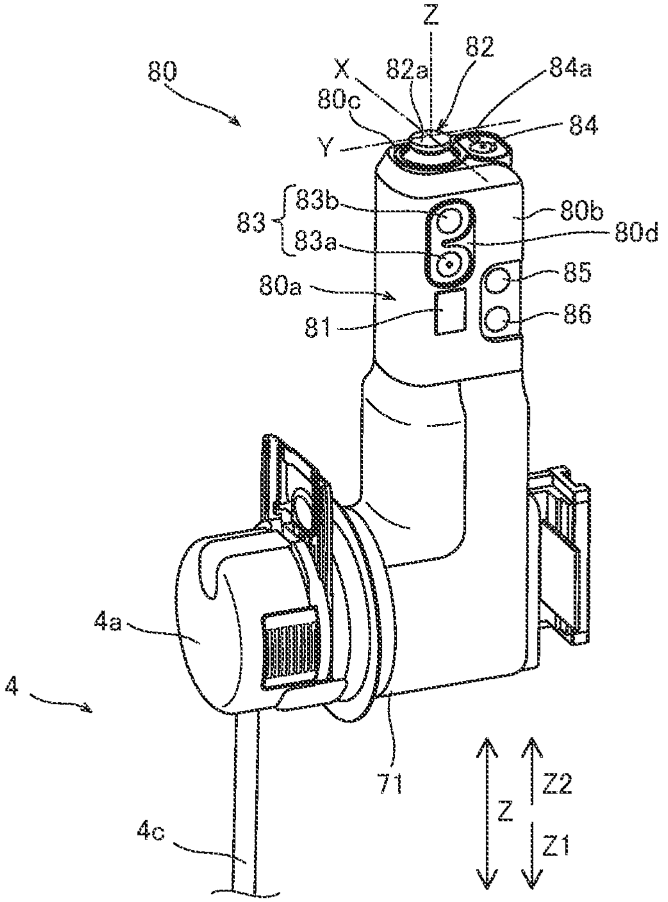
FIG. 5 is a perspective view showing the configuration of an arm operation unit of the medical manipulator according to the embodiment of the present disclosure.

As shown in FIG. 5, the medical manipulator 1 includes an arm operation unit 80 attached to each of the manipulator arms 60 to operate the manipulator arm 60. The arm operation unit 80 includes an enable switch 81, a joystick 82, and a switch unit 83. The enable switch 81 enables or disables movement of the manipulator arm 60 by the joystick 82 and the switch unit 83. The enable switch 81 enables movement of the surgical instrument 4 by the manipulator arm 60 when the enable switch 81 is pressed by an operator (such as a nurse or an assistant) grasping the arm operation unit 80.

The switch unit 83 includes a switch 83*a* to move the surgical instrument 4 in the direction in which the surgical instrument 4 is inserted into the patient P, along the longitudinal direction of the surgical instrument 4, and a switch 83*b* to move the surgical instrument 4 in a direction opposite to the direction in which the surgical instrument 4 is inserted into the patient P. Both the switch 83*a* and the switch 83*b* are push-button switches.

As shown in FIG. 5, the arm operation unit 80 includes a pivot button 85 to teach a pivot position PP that serves as a fulcrum (see FIG. 9) for movement of the surgical instrument 4 attached to the manipulator arm 60. The pivot button 85 is provided adjacent to the enable switch 81 on a surface 80*b* of the arm operation unit 80. The pivot button 85 is pressed when the tip end of the endoscope 6 (see FIG. 6) or a pivot position teaching instrument 7 (see FIG. 7) is located at a position corresponding to the insertion position of a trocar T inserted into the body surface S of the patient P such that the pivot position PP is taught and stored in the storage 32. In the teaching of the pivot position PP, the pivot position PP is set as one point (coordinates), and the direction of the surgical instrument 4 is not set.

As shown in FIG. 1, the endoscope 6 is attached to one (manipulator arm 60*b*, for example) of the plurality of manipulator arms 60, and the surgical instruments 4 other than the endoscope 6 are attached to the remaining manipulator arms 60 (manipulator arms 60*a*, 60*c*, and 60*d*, for example). Specifically, in surgery, the endoscope 6 is attached to one of four manipulator arms 60, and the surgical instruments 4 (such as pairs of forceps) other than the endoscope 6 are attached to the three manipulator arms 60. The pivot position PP is taught with the endoscope 6 attached to the manipulator arm 60 to which the endoscope 6 is to be attached. Furthermore, the pivot positions PP are taught with the pivot position teaching instruments 7 attached to the manipulator arms 60 to which the surgical instruments 4 other than the endoscope 6 are to be attached. The endoscope 6 is attached to one of two manipulator arms 60 (manipulator arms 60*b* and 60*c*) arranged in the center among the four manipulator arms 60 arranged adjacent to each other. That is, the pivot position PP is individually set for each of the plurality of manipulator arms 60.

As shown in FIG. 5, an adjustment button 86 for optimizing the position of the manipulator arm 60 is provided on the surface 80*b* of the arm operation unit 80. After the pivot position PP for the manipulator arm 60 to which the endoscope 6 has been attached is taught, the adjustment button 86 is pressed such that the positions of the other manipulator arms 60 (arm base 50) are optimized.

Figure 8:
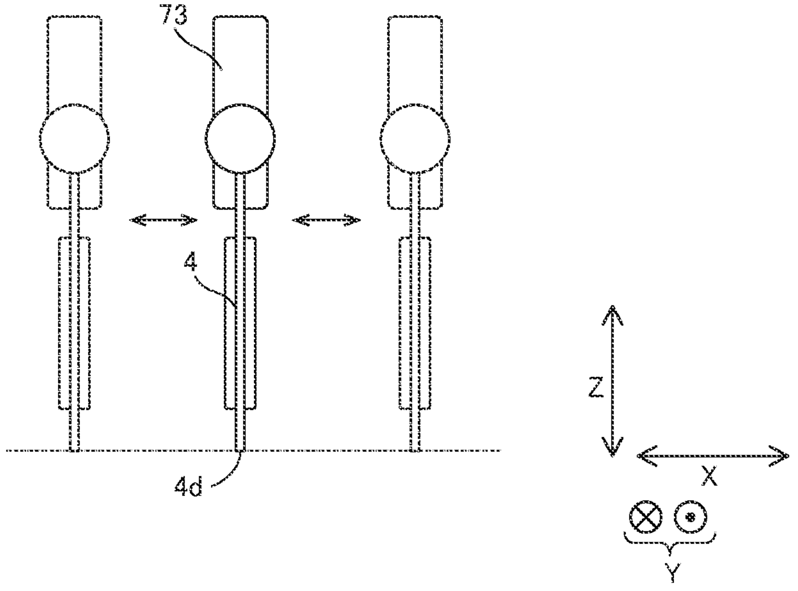
FIG. 8 is a diagram for illustrating translation of the manipulator arm.
Figure 9:
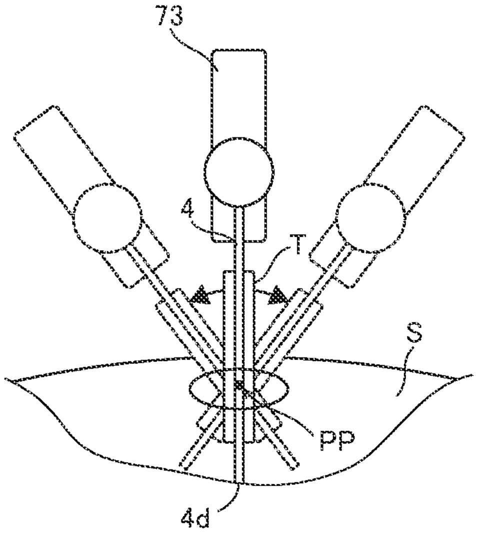
FIG. 9 is a diagram for illustrating rotation of the manipulator arm.

As shown in FIG. 5, the arm operation unit 80 includes a mode switching button 84 to switch between a mode for translating the surgical instrument 4 attached to the manipulator arm 60 (see FIG. 8) and a mode for rotationally moving the surgical instrument 4 attached to the manipulator arm 60 (see FIG. 9). Furthermore, a mode indicator 84*a* is provided in the vicinity of the mode switching button 84. The mode indicator 84*a* indicates a switched mode. Specifically, the mode indicator 84*a* is turned on (rotational movement mode) or off (translational mode) to indicate a current mode (translational mode or rotational movement mode).

The mode indicator 84*a* also serves as a pivot position indicator that indicates that the pivot position PP has been taught.

As shown in FIG. 8, in the mode for translating the manipulator arm 60, the manipulator arm 60 is moved such that the tip end 4*d* of the surgical instrument 4 moves on an X-Y plane. As shown in FIG. 9, in the mode for rotationally moving the manipulator arm 60, when the pivot position PP is not taught, the manipulator arm 60 is moved such that the surgical instrument 4 rotationally moves about the pair of forceps 4*b*, and when the pivot position PP is taught, the manipulator arm 60 is moved such that the surgical instrument 4 rotationally moves about the pivot position PP as a fulcrum. The surgical instrument 4 is rotationally moved while the shaft 4*c* of the surgical instrument 4 is inserted into the trocar T.

Figure 10:
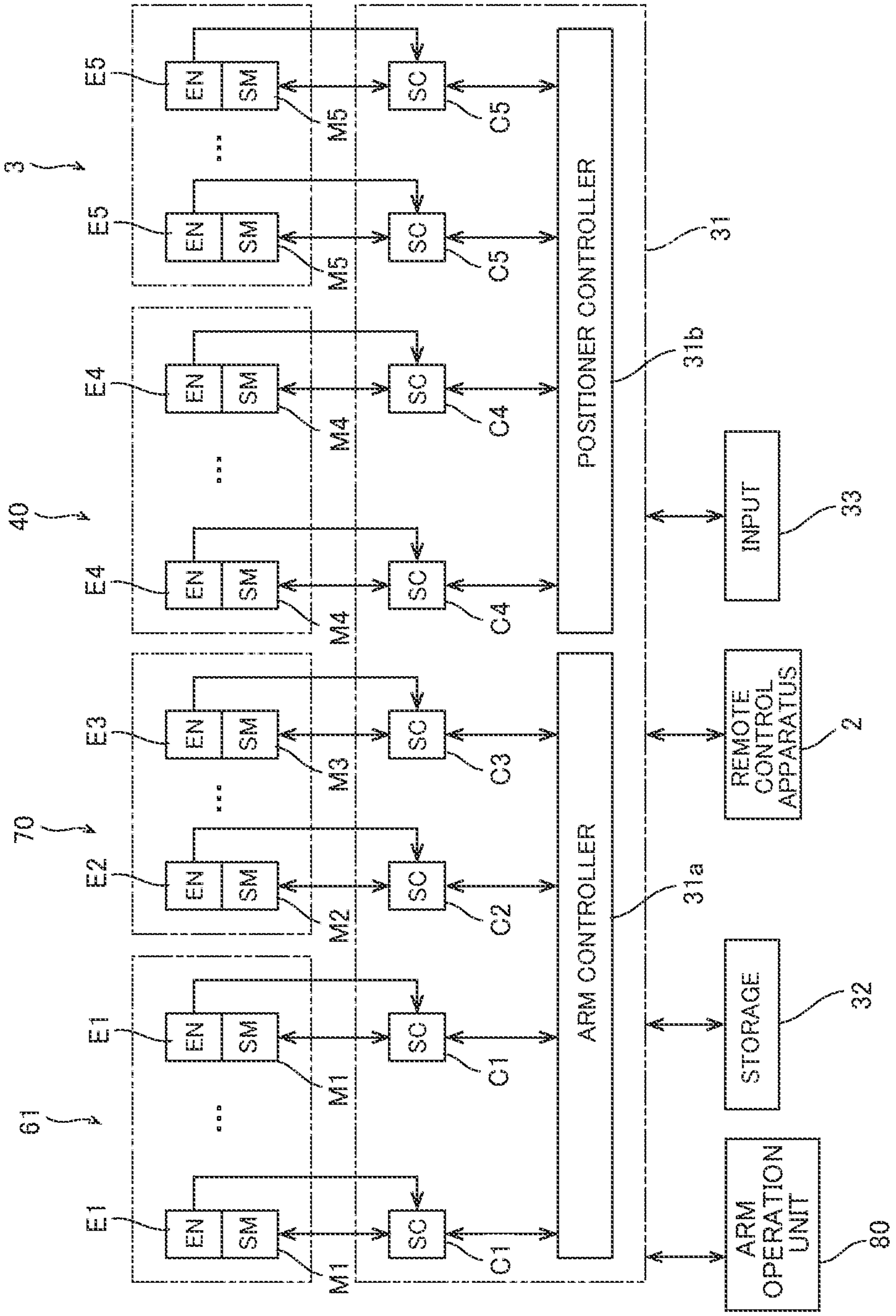
FIG. 10 is a block diagram showing the configuration of a controller of the medical manipulator according to the embodiment of the present disclosure.

As shown in FIG. 10, the manipulator arm 60 includes a plurality of servomotors M1, encoders E1, and speed reducers (not shown) so as to correspond to a plurality of joints 64 of the arm portion 61. The encoders E1 detect the rotation angles of the servomotors M1. The speed reducers slow down rotation of the servomotors M1 to increase the torques.

As shown in FIG. 10, the translation mechanism 70 includes the servomotors M2 to rotate the rotary bodies provided in the driven unit 4*a* of the surgical instrument 4, a servomotor M3 to translate the surgical instrument 4, encoders E2 and E3, and speed reducers (not shown). The encoders E2 and E3 detect the rotation angles of the servomotors M2 and M3, respectively. The speed reducers slow down rotation of the servomotors M2 and M3 to increase the torques.

The positioner 40 includes a plurality of servomotors M4, encoders E4, and speed reducers (not shown) so as to correspond to a plurality of joints 43 of the positioner 40. The encoders E4 detect the rotation angles of the servomotors M4. The speed reducers slow down rotation of the servomotors M4 to increase the torques.

The medical cart 3 includes servomotors M5 to drive a plurality of front wheels (not shown) of the medical cart 3, respectively, encoders E5, and speed reducers (not shown). The encoders E5 detect the rotation angles of the servomotors M5. The speed reducers slow down rotation of the servomotors M5 to increase the torques.

The controller 31 of the medical cart 3 includes an arm controller 31*a* to control movement of the plurality of manipulator arms 60 based on commands, and a positioner controller 31*b* to control movement of the positioner 40 and driving of the front wheels (not shown) of the medical cart 3 based on commands. Servo controllers C1 that control the servomotors M1 to drive the manipulator arm 60 are electrically connected to the arm controller 31*a*. The encoders E1 that detect the rotation angles of the servomotors M1 are electrically connected to the servo controllers C1.

Servo controllers C2 that control the servomotors M2 to drive the surgical instrument 4 are electrically connected to the arm controller 31*a*. The encoders E2 that detect the rotation angles of the servomotors M2 are electrically connected to the servo controllers C2. A servo controller C3 that controls the servomotor M3 to translate the translation mechanism 70 is electrically connected to the arm controller 31*a*. The encoder E3 that detects the rotation angle of the servomotor M3 is electrically connected to the servo controller C3.

An operation command input to the remote control apparatus 2 is input to the arm controller 31*a*. The arm controller 31*a* generates position commands based on the input operation command and the rotation angles detected by the encoders E1 (E2, E3) and outputs the position commands to the servo controllers C1 (C2, C3). The servo controllers C1 (C2, C3) generate torque commands based on the position commands input from the arm controller 31*a* and the rotation angles detected by the encoders E1 (E2, E3), and output the torque commands to the servomotors M1 (M2, M3). Thus, the manipulator arm 60 is moved according to the operation command input to the remote control apparatus 2.

Figure 11:
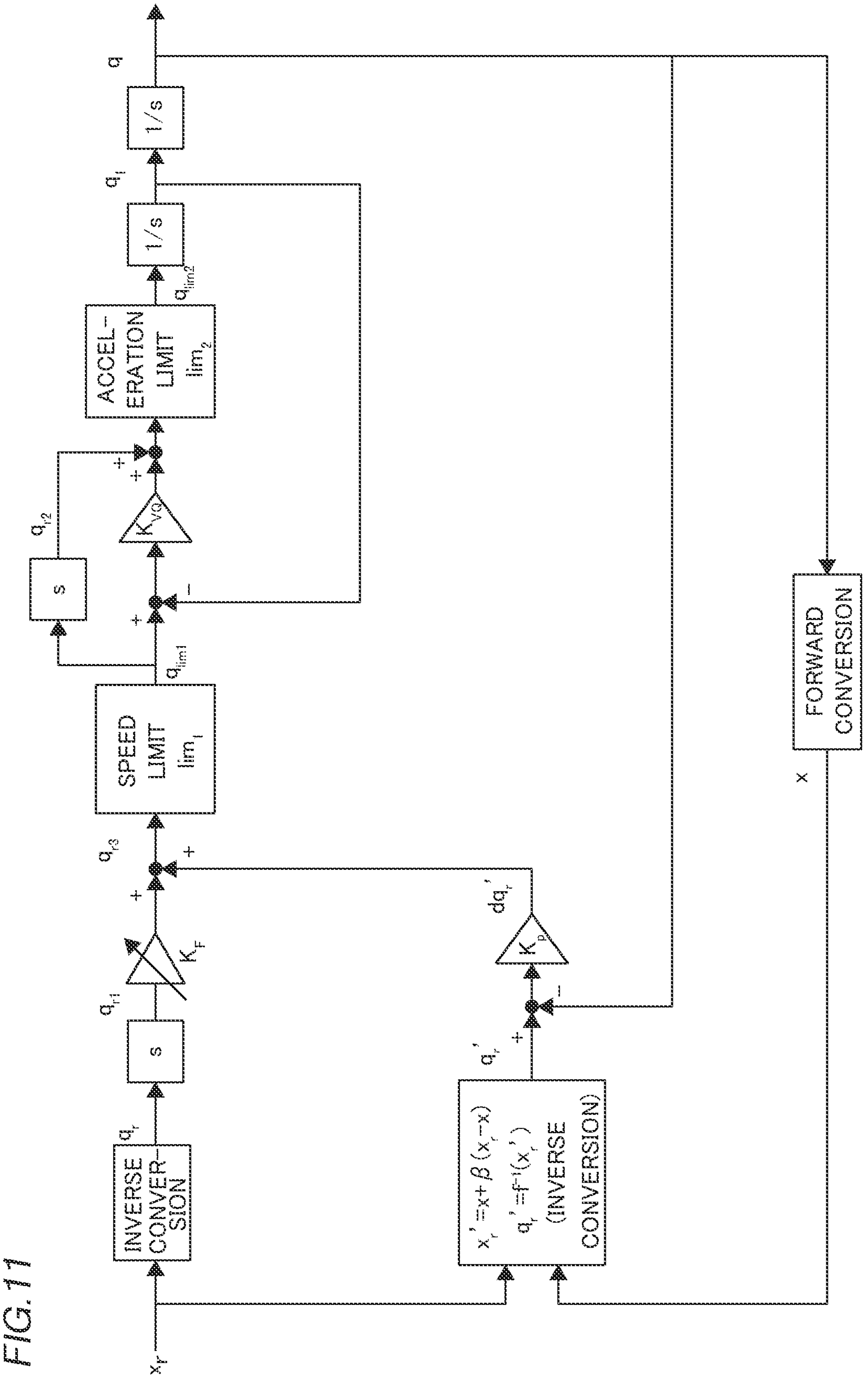
FIG. 11 is a block diagram showing the configuration of the controller according to the embodiment of the present disclosure.

Specifically, in this embodiment, as shown in FIG. 11, the controller 31 calculates a speed command value $q_{r1}$ and an acceleration command value $q_{r2}$ for operating the surgical instrument 4 based on an operation (input position command value $x_r$) received by the operation manipulator arms 21 of the remote control apparatus 2, and controls the operation of the surgical instrument 4 based on the speed command value $q_{r1}$ and the acceleration command value $q_{r2}$. Then, the controller 31 limits the speed command value $q_{r1}$ (a speed command value $q_{r3}$ to which a correction command value $$dq'_r$$

described below has been added when the correction command value $$dq'_r$$

is not 0) within a range of a speed limit value $lim_1$, and limits the acceleration command value $q_{r2}(q_{r2}+(q_{lim1}-q_1)\times K_{vp}$ when $(q_{lim1}-q_1)$ described below is not 0) within a range of an acceleration limit value $lim_2$.

More specifically, the controller 31 performs conversion (inverse conversion) using inverse kinematics on the operation (input position command value $x_r$) received by the operation manipulator arms 21 of the remote control apparatus 2 to calculate an operation command value $q_r$, and differentiates the operation command value $q_r$ to calculate the speed command value $q_{r1}$. Then, the controller 31 limits the speed command value $q_{r1}$ (specifically, the speed command value $q_{r3}$ to which the correction command value $$dq'_r$$

has been added) within the range of the speed limit value $lim_1$. The speed limit value $lim_1$ is predetermined according to the specifications of the servomotors M1, for example.

Furthermore, the controller 31 differentiates the speed command value $q_{lim1}$ limited within the range of the speed limit value $lim_1$ to calculate the acceleration command value $q_{r2}$. Moreover, the controller 31 feeds back the speed command value $q_1$ described below and subtracts it from the speed command value $q_{lim1}$ limited within the range of the speed limit value $lim_1$. The controller 31 multiplies the subtracted value $(q_{lim1}-q_1)$ by the gain $K_{vp}$, and adds the multiplied value $((q_{lim1}-q_1)\times K_{vp})$ to the acceleration command value $q_{r2}$. Then, the controller 31 limits the added value $(q_{r2}+(q_{lim1}-q_1)\times K_{vp})$ within the range of the acceleration limit value $lim_2$.

Then, the controller 31 integrates the acceleration command value $q_{lim2}$ limited within the range of the acceleration limit value $lim_2$ to calculate the speed command value $q_1$. Furthermore, the controller 31 integrates the speed command value $q_1$ to calculate an operation command value q.

The above control by the controller 31 is performed for each axis of the manipulator arm 60.

In this embodiment, the controller 31 calculates the speed command value $q_{r1}$ and the acceleration command value $q_{r2}$ for each axis of the plurality of joints 64. Based on the speed command value $q_{r1}$ and the acceleration command value $q_{r2}$ for the axis with the largest limited amounts among the axes of the plurality of joints 64, the controller 31 limits the speed command values $q_{r1}$ and the acceleration command values $q_{r2}$ for the remaining axes.

Specifically, in this embodiment, the controller 31 limits the speed command values $q_{r1}$ for the remaining axes by dividing the speed command values $q_{r1}$ for the remaining axes by a speed excess ratio of an axis with the largest speed excess ratio with respect to the speed limit value lime among the axes of the plurality of joints 64 for which the speed command values $q_{r1}$ have been calculated. More specifically, a maximum speed excess ratio $\alpha_1$ is calculated based on the following mathematical formula 1:

$$\alpha_1 = \max\left(\frac{|q_{r1i}|}{\lim_{1i}}, 1\right) \quad \text{Mathematical Formula 1}$$

where $q_{r1i}$ represents the speed command value $q_{r1}$ for each axis before being limited. The number of axes of the manipulator arm 60 is twelve including the axes of the arm portion 61 and the axes (linear motion axis and forceps axis) of the translation mechanism 70. In this case, i is any value from 1 to 12. Furthermore, $lim_{1i}$ represents a speed limit value for each axis. The speed excess ratio $\alpha_1$ is a value of 1 or more. The speed excess ratio $\alpha_1$ is 1 when none of the speed command values $q_{r1i}$ for the respective axes exceeds the speed limit value $lim_{1i}$. The above i may be set to 8 in consideration of only the axes of the arm portion 61 and the linear motion axis of the translation mechanism 70.

Then, a limited speed command value $q_{lim1i}$ is calculated by the following mathematical formula 2.

$$q_{lim1i} = \frac{q_{r1i}}{\alpha_1} \quad \text{Mathematical Formula 2}$$

In this embodiment, the acceleration command values $q_{r2}$ for the remaining axes are limited by dividing the acceleration command values $q_{r2}$ for the remaining axes by an acceleration excess ratio of an axis with the largest acceleration excess ratio with respect to the acceleration limit value $lim_2$ among the axes of the plurality of joints 64 for which the acceleration command values $q_{r2}$ have been calculated. Specifically, a maximum acceleration excess ratio $\alpha_2$ is calculated based on the following mathematical formula 3:

$$\alpha_2 = \max\left(\frac{|q_{r2i}|}{\lim_{2i}}, 1\right) \quad \text{Mathematical Formula 3}$$

where $q_{r2i}$ represents the acceleration command value $q_{r2}$ for each axis before being limited, and $lim_{2i}$ represents an acceleration limit value for each axis. The acceleration excess ratio $\alpha_2$ is a value of 1 or more. The acceleration excess ratio $\alpha_2$ is 1 when none of the acceleration command values $q_{r2i}$ for the respective axes exceeds the acceleration limit value $lim_{2i}$.

Then, a limited acceleration command value $q_{lim2i}$ is calculated by the following mathematical formula 4.

$$q_{lim2i} = \frac{q_{r2i}}{\alpha_2} \quad \text{Mathematical Formula 4}$$

An image of limitation of the speed command value $q_{r1}$ is now described with reference to FIGS. 12 and 13. An image of limitation of the acceleration command value $q_{r2}$ is similar.

Figure 12:
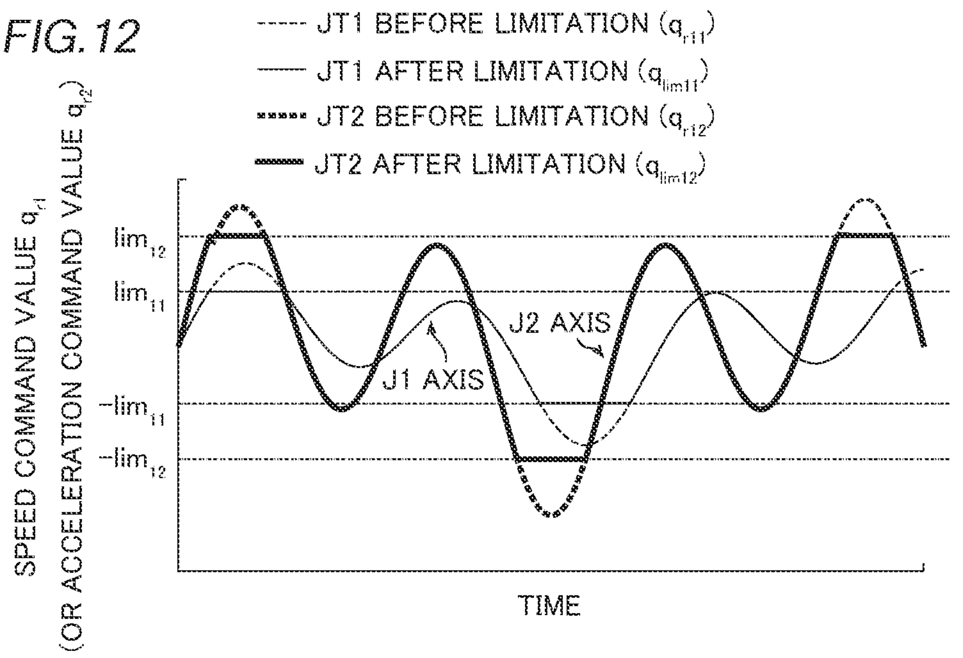
FIG. 12 is an image diagram of a limited speed command value (or acceleration command value) according to a comparative example.

FIG. 12 is an image diagram showing limitation of a speed command value $q_{r1}$ according to a comparative example, and shows an image of limitation of speed command values of two axes (a J1 axis and a J2 axis) of the arm portion 61 as an example. Specifically, FIG. 12 shows a speed command value $q_{r11}$ (thin dotted line) for the J1 axis before being limited, a speed command value $q_{lim11}$ (thin solid line) for the J1 axis after being limited, a speed command value $q_{r12}$ (thick dotted line) for the J2 axis before being limited, and a speed command value $q_{lim12}$ (thick solid line) for the J2 axis after being limited. The speed limit value for the J1 axis is set to $lim_{11}$, and the speed limit value for the J2 axis is set to $lim_{12}$. As shown in FIG. 12, the speed command value $q_{r11}$ for the J1 axis is limited within a range of the speed limit value $lim_{11}$ ($-lim_{11}$ or more and $lim_{11}$ or less). The speed command value $q_{r12}$ for the J2 axis is limited within a range of the speed limit value $lim_{12}$ ($-lim_{12}$ or more and $lim_{12}$ or less). Thus, when the speed command values $q_{r11}$ and $q_{r12}$ are individually limited for the respective axes, the relationship between the speed command value $q_{lim11}$ after limitation and the speed command value $q_{lim12}$ after limitation changes from the relationship between the speed command value $q_{r11}$ before the limitation and the speed command value $q_{r12}$ before the limitation.

For example, the speed command values $q_{r11}$ and $q_{r12}$ before limitation are assumed to be 10 and 8, respectively. Assuming that the speed limit value $lim_{11}$ and the speed limit value $lim_{12}$ are 2, the speed command values $q_{lim11}$ and $q_{lim12}$ after limitation are both 2. That is, a ratio between the speed command value $q_{r11}$ and the speed command value $q_{r12}$ before limitation is 10:8 while a ratio between the speed command value $q_{lim11}$ and the speed command value $q_{lim12}$ after limitation is 2:2. Therefore, the pivot position PP is disadvantageously deviated.

Figure 13:
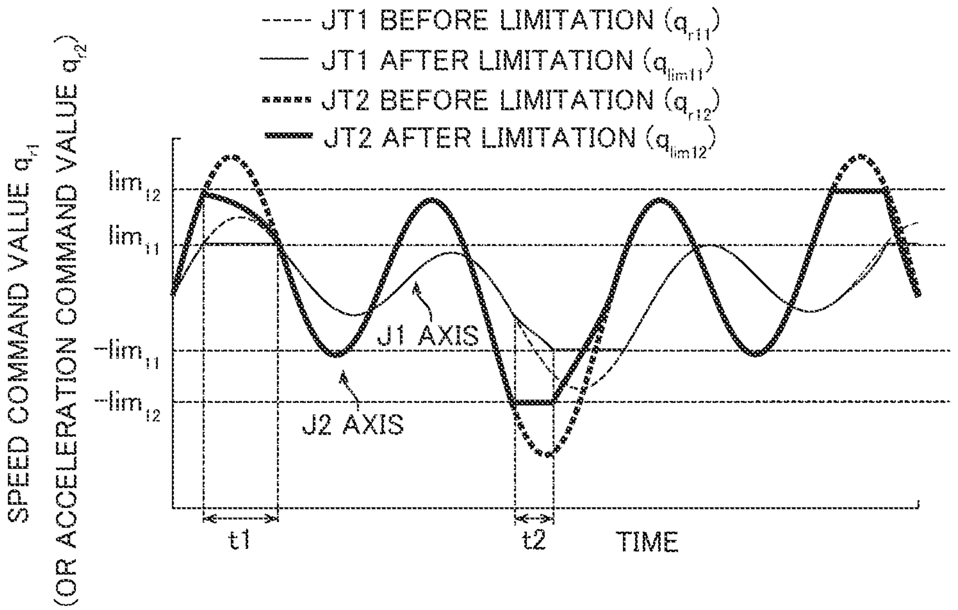
FIG. 13 is an image diagram of a limited speed command value (or acceleration command value) according to the embodiment of the present disclosure.

FIG. 13 is an image diagram showing limitation of the speed command value $q_{r1}$ according to this embodiment. In FIG. 13, the speed command value $q_{r11}$ for the J1 axis and the speed command value $q_{r12}$ for the J2 axis are limited based on the above mathematical formulas 1 and 2. For example, in a period t1, the speed excess ratio of the speed command value $q_{r11}$ for the J1 axis increases, and the speed command value $q_{r12}$ for the J2 axis is limited by being divided by the speed excess ratio of the J1 axis. Thus, the speed command value $q_{lim12}$ after limitation does not remain constant as shown in FIG. 12, but smoothly changes so as to gradually decrease. For example, in a period t2, the speed excess ratio of the speed command value $q_{r12}$ for the J2 axis increases, and the speed command value $q_{r11}$ for the J1 axis is limited by being divided by the speed excess ratio of the J2 axis. Thus, the speed command value $q_{lim11}$ after limitation does not remain constant as shown in FIG. 12, but smoothly changes so as to gradually decrease. Thus, when the speed command values $q_{r11}$ and $q_{r12}$ are limited for the respective axes based on the above mathematical formulas 1 and 2, the relationship between the speed command values $q_{r11}$ and $q_{r12}$ before limitation is maintained constant.

For example, the speed command value $q_{r11}$ and the speed command value $q_{r12}$ before limitation are assumed to be 10 and 8, respectively. Assuming that the speed limit value $lim_{11}$ and the speed limit value $lim_{12}$ are 2, the speed excess ratio of the J1 axis is 5 (=10/2), the speed excess ratio of the J1 axis is 4 (=8/2), and $\alpha_1$ is 5 based on the above mathematical formula 1. Then, a ratio between the speed command value $q_{lim11}$ and the speed command value $q_{lim12}$ after limitation is 2:8/5 based on the above mathematical formula 2, and a ratio (10:8) before limitation is maintained. Thus, a deviation of the pivot position PP is reduced or prevented.

In this embodiment, as shown in FIG. 11, the controller 31 calculates the operation command value q based on the speed command value $q_{lim1}$ limited within the range of the speed limit value $lim_1$ and the acceleration command value $q_{lim2}$ limited within the range of the acceleration limit value $lim_2$. Then, based on the calculated operation command value q, the controller 31 calculates the correction command value $dq_r'$ for correcting the deviation of the pivot position PP, which is a fulcrum for rotational movement of the surgical instrument 4.

Specifically, in this embodiment, the operation manipulator arms 21 receive an input position command value $x_r$ for the surgical instrument 4. The controller 31 feeds back the calculated operation command value q. Then, the controller 31 performs conversion (forward conversion) using forward kinematics on the fed-back operation command value q to calculate a post-forward-kinematics-conversion command value x. Furthermore, the controller 31 performs conversion (inverse conversion) using inverse kinematics on $$x_r'$$

calculated using the input position command value $x_r$ and the post-forward-kinematics-conversion command value x to calculate a post-inverse-kinematics-conversion command value $$q_r'.$$

Then, the controller 31 calculates the correction command value $$dq_r'$$

for correcting the deviation of the pivot position PP based on the operation command value q and the post-inverse-kinematics-conversion command value $$q_r'.$$

More specifically, the controller 31 calculates the post-inverse-kinematics-conversion command value $$q_r'$$

based on the following mathematical formula 5:

$$x_r' = x + \beta(x_r - x) \qquad \text{Mathematical Formula 5}$$

$$q_r' = f^{-1}(x_r')$$

where x represents the current position of the tip end of the pair of forceps 4b, β represents a gain, and $f^{-1}$ represents conversion using inverse kinematics.

Then, the controller 31 subtracts the operation command value q from the post-inverse-kinematics-conversion command value $$q_r'.$$

Furthermore, the controller 31 multiplies the subtracted value by a gain $K_p$ to calculate the correction command value $$dq'_r$$

for correcting the deviation of the pivot position PP.

Then, in this embodiment, the controller 31 adds the correction command value $$dq'_r$$

to the speed command value $q_{r1}$ before being limited within the range of the speed limit value $lim_1$.

In this embodiment, the controller 31 multiplies the calculated speed command value $q_{r1}$ by a gain $K_F$ of a feedforward control. Then, the controller 31 sets the gain $K_F$ of the feedforward control based on a difference (distance L) between a target value, which is a value of a target position for movement of the surgical instrument 4, and a current value, which is a value of the current position of the surgical instrument 4, so as to increase the contribution of a feedback control relative to the contribution of the feedforward control to the speed command value $q_{r1}$. The distance L between the target value and the current value is a distance L between a value of the target position of the surgical instrument 4 on the base side (on the tip end side of the arm portion 61) and a value of the current position of the surgical instrument 4, for example. As the distance L, a distance between a target axis value and a current axis value may be applied.

Figure 14:
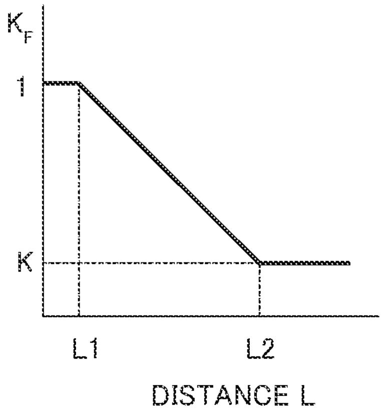
FIG. 14 is a diagram for illustrating a gain of a feedforward control according to the embodiment of the present disclosure.
Figure 15:
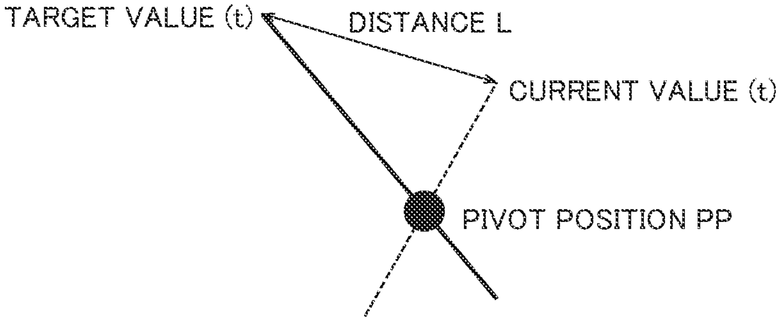
FIG. 15 is a diagram (1) showing a target value and a current value of a surgical instrument.

Specifically, in this embodiment, as shown in FIG. 14, the gain $K_F$ linearly decreases as the difference (distance L; see FIG. 15) between the target value and the current value increases. For example, the gain $K_F$ is set to 1 when the difference (distance L) between the target value and the current value is less than L1. When the distance L exceeds L2, the gain $K_F$ is set to K (a value smaller than 1). When the distance L is equal to or greater than L1 and equal to or less than L2, the gain $K_F$ is linearly interpolated between K and 1 according to the distance L.

Figure 16:
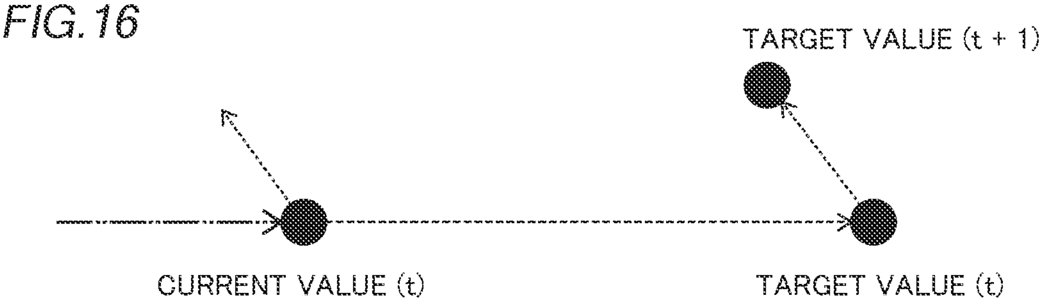
FIG. 16 is a diagram (2) showing the target value and the current value of the surgical instrument.

As shown in FIG. 16, the deviation of the pivot position PP does not occur during the movement from the target value (t), which is the value of the target position of the surgical instrument 4, to a target value (t+1) by the feedforward control. Note that t and t+1 represent time. On the other hand, the speed command value $q_{r1}$ and the acceleration command value $q_{r2}$ are limited such that a delay of x occurs with respect to the input position command value $x_r$. Thus, when each axis is moved by the same amount by the feedforward control at the current position (current value (t)), the pivot position PP is deviated. Therefore, the gain $K_F$ of the feedforward control is decreased according to the magnitude of the distance L to decrease the contribution of the feedforward control such that the deviation of the pivot position PP is reduced or prevented.

As shown in FIG. 10, the controller 31 (arm controller 31*a*) operates the manipulator arm 60 based on an input signal from the joystick 82 of the arm operation unit 80. Specifically, the arm controller 31*a* generates position commands based on the input signal (operation command) input from the joystick 82 and the rotation angles detected by the encoders E1, and outputs the position commands to the servo controllers C1. The servo controllers C1 generate torque commands based on the position commands input from the arm controller 31*a* and the rotation angles detected by the encoders E1, and output the torque commands to the servomotors M1. Thus, the manipulator arm 60 is moved according to the operation command input to the joystick 82.

The controller 31 (arm controller 31*a*) operates the manipulator arm 60 based on an input signal from the switch unit 83 of the arm operation unit 80. Specifically, the arm controller 31*a* generates a position command based on the input signal (operation command) input from the switch unit 83 and the rotation angle detected by the encoders E1 or the encoder E3, and outputs the position command to the servo controllers C1 or the servo controller C3. The servo controllers C1 or the servo controller C3 generates a torque command based on the position command input from the arm controller 31*a* and the rotation angle detected by the encoders E1 or the encoder E3, and outputs the torque command to the servomotors M1 or the servomotor M3. Thus, the manipulator arm 60 is moved according to the operation command input to the switch unit 83.

As shown in FIG. 10, servo controllers C4 that control the servomotors M4 to move the positioner 40 are electrically connected to the positioner controller 31*b*. The encoders E4 that detect the rotation angles of the servomotors M4 are electrically connected to the servo controllers C4. Servo controllers C5 that control the servomotors M5 to drive the front wheels (not shown) of the medical cart 3 are electrically connected to the positioner controller 31*b*. The encoders E5 that detect the rotation angles of the servomotors M5 are electrically connected to the servo controllers C5.

An operation command related to setting of a preparation position, for example, is input from the input 33 to the positioner controller 31*b*. The positioner controller 31*b* generates position commands based on the operation command input from the input 33 and the rotation angles detected by the encoders E4, and outputs the position commands to the servo controllers C4. The servo controllers C4 generate torque commands based on the position commands input from the positioner controller 31*b* and the rotation angles detected by the encoders E4, and output the torque commands to the servomotors M4. Thus, the positioner 40 is moved according to the operation command input to the input 33. Similarly, the positioner controller 31*b* moves the medical cart 3 according to an operation command from the input 33.

Control Method of Surgical System

Figure 17:
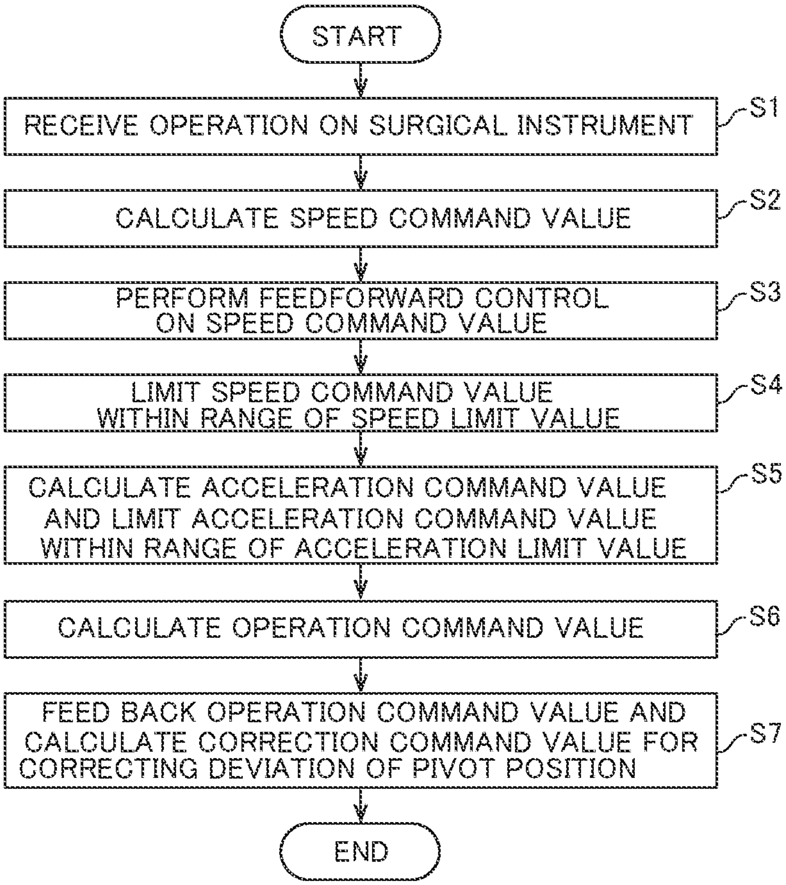
FIG. 17 is a flowchart for illustrating a control method of the surgical system according to the embodiment of the present disclosure.

A control method of the surgical system 100 is now described with reference to FIG. 17.

First, in step S1, the controller 31 receive an operation on the surgical instrument 4.

Then, in step S2, the controller 31 calculates the speed command value $q_{r1}$ for operating the surgical instrument 4 based on the received operation.

Then, in step S3, the controller 31 multiplies the calculated speed command value $q_{r1}$ by the gain $K_F$ of the feedforward control.

Then, in step S4, the controller 31 limits the speed command value $q_{r1}$ multiplied by the gain $K_F$ of the feedforward control within the range of the speed limit value $lim_1$.

Then, in step S5, the controller 31 calculates the acceleration command value $q_{r2}$ by differentiating the speed command value $q_{lim1}$ limited within the range of the speed limit value $lim_1$, and limits the acceleration command value $q_{r2}$ within the range of the acceleration limit value $lim_2$.

Then, in step S6, the controller 31 calculates the operation command value q based on the speed command value $q_{lim1}$ limited within the range of the speed limit value $lim_1$ and the acceleration command value $q_{lim2}$ limited within the range of the acceleration limit value $lim_2$, and controls the operation of the surgical instrument 4 based on the operation command value q.

Then, in step S7, the controller 31 feeds back the calculated operation command value q. Then, the controller 31 calculates the correction command value $$dq_r'$$

for correcting the deviation of the pivot position PP based on the fed-back operation command value q and the input position command value $x_r$. The controller 31 adds the calculated correction command value $$dq_r'$$

to the speed command value $q_{r1}$ before being limited within the range of the speed limit value $lim_1$.

The operations in step S1 to step S7 described above are constantly performed during the operation of the manipulator arm 60, and are performed for each of the plurality of manipulator arms 60.

Advantages of this Embodiment

According to this embodiment, the following advantages are achieved.

Advantages of Surgical Robot and Medical Manipulator

According to this embodiment, as described above, the controller 31 is configured or programmed to limit the speed command value $q_{r1}$ within the range of the speed limit value $lim_1$, and limit the acceleration command value $q_{r2}$ within the range of the acceleration limit value $lim_2$. Accordingly, even when the amount of operation received by the operation manipulator arms 21 is relatively large, both the speed command value $q_{r1}$ and the acceleration command value $q_{r2}$ are limited, and thus an increase in the amount of movement of the manipulator arm 60 per unit time is reduced or prevented. Therefore, rotation of the servomotors M1 provided at the joints 64 of the manipulator arm 60 at an excessively high speed is reduced or prevented, and thus components of the joints 64 of the manipulator arm 60, such as the servomotors M1, can be protected. Furthermore, an increase in the amount of movement of the manipulator arm 60 per unit time is reduced or prevented, and thus vibrations of the manipulator arm 60 due to the large amount of movement of the manipulator arm 60 per unit time can be reduced or prevented. Consequently, the components of the joints 64 of the manipulator arm 60 can be protected, and the vibrations of the manipulator arm 60 can be reduced or prevented.

According to this embodiment, as described above, the manipulator arm 60 includes the plurality of joints 64, and the controller 31 is configured or programmed to calculate the speed command value $q_{r1}$ and the acceleration command value $q_{r2}$ for each axis of the plurality of joints 64, and limit, based on the limitation ratios of the speed command value $q_{r1}$ and the acceleration command value $q_{r2}$ for the axis with the largest limited amounts of the speed command value $q_{r1}$ and the acceleration command value $q_{r2}$ among the axes of the plurality of joints 64, the speed command values $q_{r1}$ and the acceleration command values $q_{r2}$ for the remaining axes. In the surgical system 100, the pivot position PP that serves as a fulcrum for rotational movement of the surgical instrument 4 is set, and the speed command value $q_{r1}$ and the acceleration command value $q_{r2}$ for each axis are set so as not to deviate the pivot position PP. That is, the relationship between the speed command values $q_{r1}$ for the respective axes is maintained constant, and the relationship between the acceleration command values $q_{r2}$ for the respective axes is maintained constant. However, when the speed command value $q_{r1}$ and the acceleration command value $q_{r2}$ are limited for each axis of the plurality of joints 64, the constant relationship between the speed command values $q_{r1}$ for the respective axes and the constant relationship between the acceleration command values $q_{r2}$ for the respective axes are broken. Therefore, as described above, the speed command values $q_{r1}$ and the acceleration command values $q_{r2}$ for the remaining axes are limited based on the limitation ratios of the speed command value $q_{r1}$ and the acceleration command value $q_{r2}$ for the axis with the largest limited amounts such that the broken constant relationship between the speed command values $q_{r1}$ for the respective axes and the broken constant relationship between the acceleration command values $q_{r2}$ for the respective axes are reduced or prevented, and thus the deviation of the pivot position PP can be reduced or prevented while the components of the joints 64 of the manipulator arm 60 are protected, and the vibrations of the manipulator arm 60 are reduced or prevented.

According to this embodiment, as described above, the controller 31 is configured or programmed to limit the speed command values $q_{r1}$ for the remaining axes by dividing the speed command values $q_{r1}$ for the remaining axes by the speed excess ratio $\alpha_1$ of the axis with the largest speed excess ratio $\alpha_1$ with respect to the speed limit value lime among the axes of the plurality of joints 64 for which the speed command values $q_{r1}$ have been calculated, and limit the acceleration command values $q_{r2}$ for the remaining axes by dividing the acceleration command values $q_{r2}$ for the remaining axes by the acceleration excess ratio $\alpha_2$ of the axis with the largest acceleration excess ratio $\alpha_2$ with respect to the acceleration limit value $lim_2$ among the axes of the plurality of joints 64 for which the acceleration command values $q_{r2}$ have been calculated. Accordingly, the speed command values $q_{r1}$ for the remaining axes are divided by the speed excess ratio $\alpha_1$ of the axis with the largest speed excess ratio $\alpha_1$, and thus the speed command values $q_{r1}$ for the respective axes can be limited while the relationship between the speed command values $q_{r1}$ for the respective axes is maintained constant. Furthermore, the acceleration command values $q_{r2}$ for the remaining axes are divided by the acceleration excess ratio $\alpha_2$ of the axis with the largest acceleration excess ratio $\alpha_2$ with respect to the acceleration limit value $lim_2$, and thus the acceleration command values $q_{r2}$ for the respective axes can be limited while the relationship between the acceleration command values $q_{r2}$ for the respective axes is maintained constant.

According to this embodiment, as described above, the controller 31 is configured or programmed to calculate the operation command value q based on the speed command value $q_{lim1}$ limited within the range of the speed limit value lime and the acceleration command value $q_{lim2}$ limited within the range of the acceleration limit value $\lim_2$, and calculate the correction command value $$dq_r'$$

to correct the deviation of the pivot position PP that serves as a fulcrum for rotational movement of the surgical instrument 4 based on the calculated operation command value q. Accordingly, even when the pivot position PP is deviated due to the limitation of the speed command value $q_{r1}$ and the acceleration command value $q_{r2}$, the operation command value q is corrected using the correction command value $$dq_r'$$

for each axis such that the deviation of the pivot position PP can be corrected for each axis.

According to this embodiment, as described above, the controller 31 is configured or programmed to add the correction command value $$dq_r'$$

to the speed command value $q_{r1}$ before being limited within the range of the speed limit value $\lim_1$. Accordingly, the speed command value $q_{r1}$ can be limited in consideration of the deviation of the pivot position PP.

According to this embodiment, as described above, the controller 31 is configured or programmed to feed back the calculated operation command value q, calculate the post-inverse-kinematics-conversion command value $$q_r'$$

by performing conversion using inverse kinematics on the fed-back operation command value q (specifically, $x_r'$ based on the operation command value q), and calculate the correction command value $$dq_r'$$

based on the post-inverse-kinematics-conversion command value $$q_r'.$$

Accordingly, even when the position of the surgical instrument 4 is deviated from the target position due to the limitation of the speed command value $q_{r1}$ and the acceleration command value $q_{r2}$, the calculated operation command value q is fed back such that the positional deviation of the surgical instrument 4 can be reduced or prevented.

According to this embodiment, as described above, the operation manipulator arms 21 receive the input position command value $x_r$ for the surgical instrument 4, and the controller 31 is configured or programmed to feed back the calculated operation command value q, calculate the post-forward-kinematics-conversion command value x by performing conversion using forward kinematics on the fed-back operation command value q, calculate the post-inverse-kinematics-conversion command value $$q_r'$$

by performing conversion using inverse kinematics on the input position command value $x_r$ and the post-forward-kinematics-conversion command value x, and calculate the correction command value $$dq_r'$$

based on the operation command value q and the post-inverse-kinematics-conversion command value $$q_r'.$$

Accordingly, the operation command value q representing the displacement of the joints 64 of the manipulator arm 60 is converted into the position of the manipulator arm 60 (surgical instrument 4) using forward kinematics, and thus a feedback control based on a difference between the input position command value $x_r$ and the operation command value q can be performed based on the input position command value $x_r$ corresponding to the position of the manipulator arm 60 and the operation command value q converted into the position of the manipulator arm 60. Furthermore, the correction command value $dq_r'$ is calculated based on both the operation command value q and the post-inverse-kinematics-conversion command value $q_r'$ such that the deviation of the pivot position PP can be further reduced or prevented.

According to this embodiment, as described above, the controller 31 is configured or programmed to multiply the calculated speed command value $q_{r1}$ by the gain $K_F$ of the feedforward control, and set the gain $K_F$ of the feedforward control based on the difference (distance L) between the target value, which is the value of the target position for movement of the surgical instrument 4, and the current value, which is the value of the current position of the surgical instrument 4, so as to increase the contribution of the feedback control relative to the contribution of the feedforward control to the speed command value $q_{r1}$. While the pivot position PP is not deviated due to the feedforward control at the target position for movement of the surgical instrument 4, the pivot position PP is deviated due to the feedforward control at the current position when the target value and the current value are different from each other.

Therefore, as described above, the gain $K_F$ of the feedforward control is set so as to increase the contribution of the feedback control relative to the contribution of the feedforward control to the speed command value $q_{r1}$ such that the contribution of the feedback control is greater than that of the feedforward control, and thus the positional deviation of the surgical instrument 4 can be reduced or prevented. Thus, the deviation of the pivot position PP can be further reduced or prevented.

According to this embodiment, as described above, the gain $K_F$ decreases as the difference (distance L) between the target value and the current value increases. As the difference (distance L) between the target value and the current value increases, the deviation of the pivot position PP increases. Therefore, as described above, the gain $K_F$ is decreased as the difference (distance L) between the target value and the current value increases such that even when the difference (distance L) between the target value and the current value increases, the deviation of the pivot position PP can be effectively reduced or prevented.

According to this embodiment, as described above, the gain $K_F$ linearly decreases as the difference (distance L) between the target value and the current value increases.

Advantages of Control Method of Surgical System

According to this embodiment, as described above, the step of controlling the operation of the surgical instrument 4 based on the speed command value $q_{r1}$ and the acceleration command value $q_{r2}$ includes the step of limiting the speed command value $q_{r1}$ within the range of the speed limit value $lim_1$, and the step of limiting the acceleration command value $q_{r2}$ within the range of the acceleration limit value $lim_2$. Accordingly, even when the amount of operation received by operation manipulator arms 21 is relatively large, both the speed command value $q_{r1}$ and the acceleration command value $q_{r2}$ are limited, and thus an increase in the amount of movement of the manipulator arm 60 per unit time is reduced or prevented. Therefore, rotation of the servomotors M1 provided at the joints 64 of the manipulator arm 60 at an excessively high speed is reduced or prevented, and thus the components of the joints 64 of the manipulator arm 60, such as the servomotors M1, can be protected. Furthermore, an increase in the amount of movement of the manipulator arm 60 per unit time is reduced or prevented, and thus the vibrations of the manipulator arm 60 due to the large amount of movement of the manipulator arm 60 per unit time can be reduced or prevented. Consequently, it is possible to provide the controller 31 of the surgical system 100 capable of protecting the components of the joints 64 of the manipulator arm 60 and reducing or preventing the vibrations of the manipulator arm 60.

Modified Examples

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while the example in which the controller 31 is provided in the medical manipulator 1 has been shown in the aforementioned embodiment, the present disclosure is not limited to this. For example, the controller 31 may be provided in the remote control apparatus 2. Alternatively, the controller 31 may be provided separately from the medical manipulator 1 and the remote control apparatus 2, for example.

While the example in which the speed command values $q_{r1}$ and the acceleration command values $q_{r2}$ for the remaining axes are limited based on the limitation ratios of the speed command value $q_{r1}$ and the acceleration command value $q_{r2}$ for the axis with the largest limited amounts among the axes of the plurality of joints 64 has been shown in the aforementioned embodiment, the present disclosure is not limited to this. For example, the speed command values $q_{r1}$ and the acceleration command values $q_{r2}$ for the remaining axes may be limited based on the limitation ratios of the speed command value $q_{r1}$ and the acceleration command value $q_{r2}$ for an axis (such as an axis with the second largest limitation ratios) other than the axis with the largest limited amounts.

While the example in which the feedforward control is performed for the calculated speed command value $q_{r1}$ has been shown in the aforementioned embodiment, the present disclosure is not limited to this. For example, the feedforward control may not be performed.

While the example in which the gain of the feedforward control linearly decreases has been shown in the aforementioned embodiment, the present disclosure is not limited to this. For example, the gain of the feedforward control may exponentially decrease.

While the example in which four manipulator arms 60 are provided has been shown in the aforementioned embodiment, the present disclosure is not limited to this. In the present disclosure, the number of manipulator arms 60 may be any number as long as at least one manipulator arm 60 is provided.

While the example in which each of the arm portion 61 and the positioner 40 includes a 7-axis articulated robot has been shown in the aforementioned embodiment, the present disclosure is not limited to this. For example, each of the arm portion 61 and the positioner 40 may include an articulated robot having an axis configuration (six axes or eight axes, for example) other than the 7-axis articulated robot.

While the example in which the medical manipulator 1 includes the medical cart 3, the positioner 40, and the arm base 50 has been shown in the aforementioned embodiment, the present disclosure is not limited to this. For example, the medical manipulator 1 may not include the medical cart 3, the positioner 40, or the arm base 50, but may include only the manipulator arms 60.

The functionality of the elements disclosed herein may be implemented using circuitry or processing circuitry that includes general purpose processors, special purpose processors, integrated circuits, application specific integrated circuits (ASICs), conventional circuitry and/or combinations thereof that are configured or programmed to perform the disclosed functionality. Processors are considered processing circuitry or circuitry as they include transistors and other circuitry therein. In the present disclosure, the circuitry, units, or means are hardware that carries out or is programmed to perform the recited functionality. The hardware may be hardware disclosed herein or other known hardware that is programmed or configured to carry out the recited functionality. When the hardware is a processor that may be considered a type of circuitry, the circuitry, means, or units are a combination of hardware and software, and the software is used to configure the hardware and/or processor.

DESCRIPTION OF REFERENCE NUMERALS

1: medical manipulator (patient-side apparatus)
2: remote control apparatus (operator-side apparatus)
4: surgical instrument
21: operation manipulator arm (operation unit)
31: controller (control device)
60: manipulator arm
64: joint
100: surgical system (robotic surgical system)
$dq_r'$: correction command value $K_F$: gain of a feedforward control
$lim_1$: speed limit value
$lim_2$: acceleration limit value
q: operation command value
$q_{r1}$: speed command value
$q_{r2}$: acceleration command value
$q_r'$: post-inverse-kinematics-conversion command value
PP: pivot position
x: post-forward-kinematics-conversion command value
$x_r$: input position command value
$\alpha_1$: speed excess ratio
$\alpha_2$: acceleration excess ratio

The invention claimed is:

1. A robotic surgical system comprising:
- a patient-side apparatus including a manipulator arm including a plurality of joints and a corresponding plurality of axes, and having a tip end side to which a surgical instrument is attached;
- an operator-side apparatus including an operation unit to receive an operation on the surgical instrument; and
- a controller configured or programmed to perform operations comprising operations to calculate, for each axis of the plurality of axes corresponding to the plurality of joints, a speed command value and an acceleration command value to operate the surgical instrument based on the received operation, and control operation of the surgical instrument based on the speed command value and the acceleration command value; wherein the controller is configured or programmed to perform operations further comprising operations to:
  - for each axis of the plurality of axes corresponding to the plurality of joints:
    - limit the speed command value to a limited speed command value within a range of speed limit values;
    - limit the acceleration command value to a limited acceleration command value within a range of acceleration limit values;
    - determine a speed excess ratio corresponding to a ratio between the calculated speed command value and the limited speed command value; and
    - determine an acceleration excess ratio corresponding to a ratio between the calculated acceleration command value and the limited acceleration command value;
  - determine a maximum speed excess ratio among the plurality of axes;
  - determine a maximum acceleration excess ratio among the plurality of axes;
  - limit the speed command values for remaining axes of the plurality of axes to the largest limited speed command value corresponding to the axis of the plurality of axes having the maximum speed excess ratio by dividing the speed command values for each of the remaining axes of the plurality of axes by the speed excess ratio;
  - limit the acceleration command values for remaining axes of the plurality of axes to the acceleration command value corresponding to the axis of the plurality of axes having the maximum acceleration excess ratio by dividing the acceleration command values for each the remaining axes of the plurality of axes by the acceleration excess ratio; and
  - the speed command values and the acceleration command values are limited, for each of the axes of the plurality of axes, to the speed command value corresponding to the axis of the plurality of axes having the maximum speed excess ratio, and the acceleration command value corresponding to the axis of the plurality of axes having the maximum acceleration excess ratio such that the amount of movement of the manipulator arm per unit time is reduced.

2. The robotic surgical system according to claim 1, wherein the controller is configured or programmed to perform operations comprising operations to:
- calculate an operation command value based on the largest limited speed command value limited within the range of the speed limit value and based on the largest limited acceleration command value limited within the range of the acceleration limit value; and
- calculate a correction command value to correct a deviation of a pivot position that serves as a fulcrum for rotational movement of the surgical instrument based on the calculated operation command value.

3. The robotic surgical system according to claim 2, wherein the controller is configured or programmed to perform operations comprising operations to add the correction command value to the speed command value before being limited within the range of the speed limit value.

4. The robotic surgical system according to claim 2, wherein the controller is configured or programmed to perform operations comprising operations to:
- feed back the calculated operation command value;
- calculate a post-inverse-kinematics-conversion command value by performing conversion using inverse kinematics on the fed-back operation command value; and
- calculate the correction command value based on the post-inverse-kinematics-conversion command value.

5. The robotic surgical system according to claim 4, wherein
- the operation unit receives an input position command value for the surgical instrument; and
- the controller is configured or programmed to perform operations comprising operations to:
  - feed back the calculated operation command value;
  - calculate a post-forward-kinematics-conversion command value by performing conversion using forward kinematics on the fed-back operation command value;
  - calculate the post-inverse-kinematics-conversion command value by performing the conversion using the inverse kinematics on the input position command value and the post-forward-kinematics-conversion command value; and
  - calculate the correction command value based on the operation command value and the post-inverse-kinematics-conversion command value.

6. The robotic surgical system according to claim 4, wherein the controller is configured or programmed to perform operations comprising operations to:
- multiply the calculated speed command value by a gain of a feedforward control; and
- set the gain of the feedforward control based on a difference between a target value, which is a value of a target position for movement of the surgical instrument, and a current value, which is a value of a current position of the surgical instrument, so as to increase a contribution of a feedback control relative to a contribution of the feedforward control to the speed command value.

7. The robotic surgical system according to claim 6, wherein the gain decreases as the difference between the target value and the current value increases.

8. The robotic surgical system according to claim 7, wherein the gain linearly decreases as the difference between the target value and the current value increases.

9. A control device of a robotic surgical system, the robotic surgical system including a patient-side apparatus including a manipulator arm including a plurality of joints and a corresponding plurality of axes, and having a tip end side to which a surgical instrument is attached, and an operator-side apparatus including an operation unit to receive an operation on the surgical instrument, the control device comprising:

a controller configured or programmed to perform operations comprising operations to calculate, for each axis of the plurality of axes corresponding to the plurality of joints, a speed command value and an acceleration command value to operate the surgical instrument based on the received operation, and control operation of the surgical instrument based on the speed command value and the acceleration command value; wherein the controller is configured or programmed to perform operations further comprising operations to:

for each axis of the plurality of axes corresponding to the plurality of joints:

limit the speed command value to a limited speed command value within a range of speed limit values; and limit the acceleration command value to a limited acceleration command value within a range of acceleration limit values;

determine a speed excess ratio corresponding to a ratio between the calculated speed command value and the limited speed command value; and determine an acceleration excess ratio corresponding to a ratio between the calculated acceleration command value and the limited acceleration command value;

determine a maximum speed excess ratio among the plurality of axes;

determine a maximum acceleration excess ratio among the plurality of axes;

limit the speed command values for remaining axes of the plurality of axes to the speed command value corresponding to the axis of the plurality of axes having the maximum speed excess ratio by dividing the speed command values for each of the remaining axes of the plurality of axes by the speed excess ratio;

limit the acceleration command values for remaining axes of the plurality of axes to the acceleration command value corresponding to the axis of the plurality of axes having the maximum acceleration excess ratio by dividing the acceleration command values for each of the remaining axes of the plurality of axes by the acceleration excess ratio; and the speed command values and the acceleration command values are limited, for each of the axes of the plurality of axes, to the speed command value corresponding to the axis of the plurality of axes having the maximum speed excess ratio, and the acceleration command value corresponding to the axis of the plurality of axes having the maximum acceleration excess ratio such that the amount of movement of the manipulator arm per unit time is reduced.

10. A control method of a robotic surgical system, the robotic surgical system including a patient-side apparatus including a manipulator arm including a plurality of joints and a corresponding plurality of axes, and having a tip end side to which a surgical instrument is attached, and an operator-side apparatus including an operation unit to receive an operation on the surgical instrument, the control method comprising:

receiving an operation on the surgical instrument; and calculating, for each axis of the plurality of axes corresponding to the plurality of joints, a speed command value and an acceleration command value to operate the surgical instrument based on the received operation, and controlling operation of the surgical instrument based on the speed command value and the acceleration command value; wherein the controlling the operation of the surgical instrument based on the speed command value and the acceleration command value includes:

for each axis of the plurality of axes corresponding to the plurality of joints:

limiting the speed command value to a limited speed command value within a range of speed limit values; and limiting the acceleration command value to a limited acceleration command value within a range of acceleration limit values;

determining a speed excess ratio corresponding to a ratio between the calculated speed command value and the limited speed command value; and determining an acceleration excess ratio corresponding to a ratio between the calculated acceleration command value and the limited acceleration command value;

determining a maximum speed excess ratio among the plurality of axes;

determining a maximum acceleration excess ratio among the plurality of axes;

limiting the speed command values for remaining axes of the plurality of axes to the speed command value corresponding to the axis of the plurality of axes having the maximum speed excess ratio by dividing the speed command values for each of the remaining axes of the plurality of axes by the speed excess ratio;

limiting the acceleration command values for remaining axes of the plurality of axes to the acceleration command value corresponding to the axis of the plurality of axes having the maximum acceleration excess ratio by dividing the acceleration command values for each of the remaining axes of the plurality of axes by the acceleration excess ratio; and the speed command values and the acceleration command values are limited, for each of the axes of the plurality of axes, to the speed command value corresponding to the axis of the plurality of axes having the maximum speed excess ratio, and the acceleration command value corresponding to the axis of the plurality of axes having the maximum acceleration excess ratio such that the amount of movement of the manipulator arm per unit time is reduced.

* * * * *